United States Patent
Dower

(10) Patent No.: US 9,078,669 B2
(45) Date of Patent: Jul. 14, 2015

(54) ORTHOPAEDIC CUTTING GUIDE INSTRUMENT

(75) Inventor: Liam Dower, Huddersfield (GB)

(73) Assignee: DEPUY INTERNATIONAL LIMITED, Leeds (GB)

(*) Notice: Subject to any disclaimer, the term of this patent is extended or adjusted under 35 U.S.C. 154(b) by 603 days.

(21) Appl. No.: 12/296,233

(22) PCT Filed: Apr. 2, 2007

(86) PCT No.: PCT/GB2007/001198
§ 371 (c)(1),
(2), (4) Date: Mar. 25, 2009

(87) PCT Pub. No.: WO2007/113534
PCT Pub. Date: Oct. 11, 2007

(65) Prior Publication Data
US 2010/0010493 A1    Jan. 14, 2010

(30) Foreign Application Priority Data
Apr. 5, 2006   (GB) .................................. 0606837.3

(51) Int. Cl.
*A61B 17/58*   (2006.01)
*A61B 17/15*   (2006.01)

(52) U.S. Cl.
CPC ............. *A61B 17/157* (2013.01); *A61B 17/155* (2013.01); *A61B 17/154* (2013.01)

(58) Field of Classification Search
USPC ...................................................... 606/87–89
See application file for complete search history.

(56) References Cited

U.S. PATENT DOCUMENTS

| | | | |
|---|---|---|---|
| 4,759,350 A * | 7/1988 | Dunn et al. ..................... 606/82 |
| 4,952,213 A * | 8/1990 | Bowman et al. ................ 606/79 |
| 5,234,433 A | 8/1993 | Bert et al. |
| 5,681,316 A * | 10/1997 | DeOrio et al. .................. 606/88 |
| 5,810,831 A | 9/1998 | D'Antonio |
| 6,884,246 B1 | 4/2005 | Sonnabend et al. |
| 2004/0039395 A1* | 2/2004 | Coon et al. ..................... 606/87 |
| 2004/0249385 A1 | 12/2004 | Faoro |
| 2005/0070910 A1 | 3/2005 | Keene |

FOREIGN PATENT DOCUMENTS

| | | |
|---|---|---|
| EP | 0947169 A | 10/1999 |
| EP | 1340468 A | 9/2003 |

(Continued)

OTHER PUBLICATIONS

PCT Written Opinion, 9 pages.
International Search Report, dated Jul. 5, 2007, 5 pages.
UK Search Report, dated Aug. 1, 2006, 3 pages.
European Search Report for EPO Application No. 07732252.7-1506 Dated Apr. 29, 2014, 5 Pages.

(Continued)

*Primary Examiner* — Nicholas Woodall

(57) ABSTRACT

A cutting guide instrument for use in a cutting step in an orthopedic surgical procedure comprises a reference component comprising a first element which can be attached or otherwise aligned relative to the bone in a predetermined arrangement and a locator arm. The invention further comprises a cutting block comprising a reference surface which can be engaged by a cutting tool to define the location and orientation of the tool during the cutting step. The cutting block further comprises at least one fixation bore for receiving a fixation pin to fix the cutting block to the bone. The locator arm can be fitted against the reference surface so that the reference component and cutting block are arranged in a predetermined manner.

1 Claim, 5 Drawing Sheets

(56) References Cited

FOREIGN PATENT DOCUMENTS

| | | | |
|---|---|---|---|
| JP | 2003525685 | A | 9/2001 |
| JP | 03525685 | A | 9/2003 |
| WO | 00/71035 | A | 11/2000 |
| WO | 0166021 | A | 9/2001 |
| WO | 0166021 | A1 | 9/2001 |

OTHER PUBLICATIONS

Japanese Examiner's Decision of Refusal for Patent Application No. 2009-503640 Dated Sep. 25, 2012, 2 Pages.

* cited by examiner

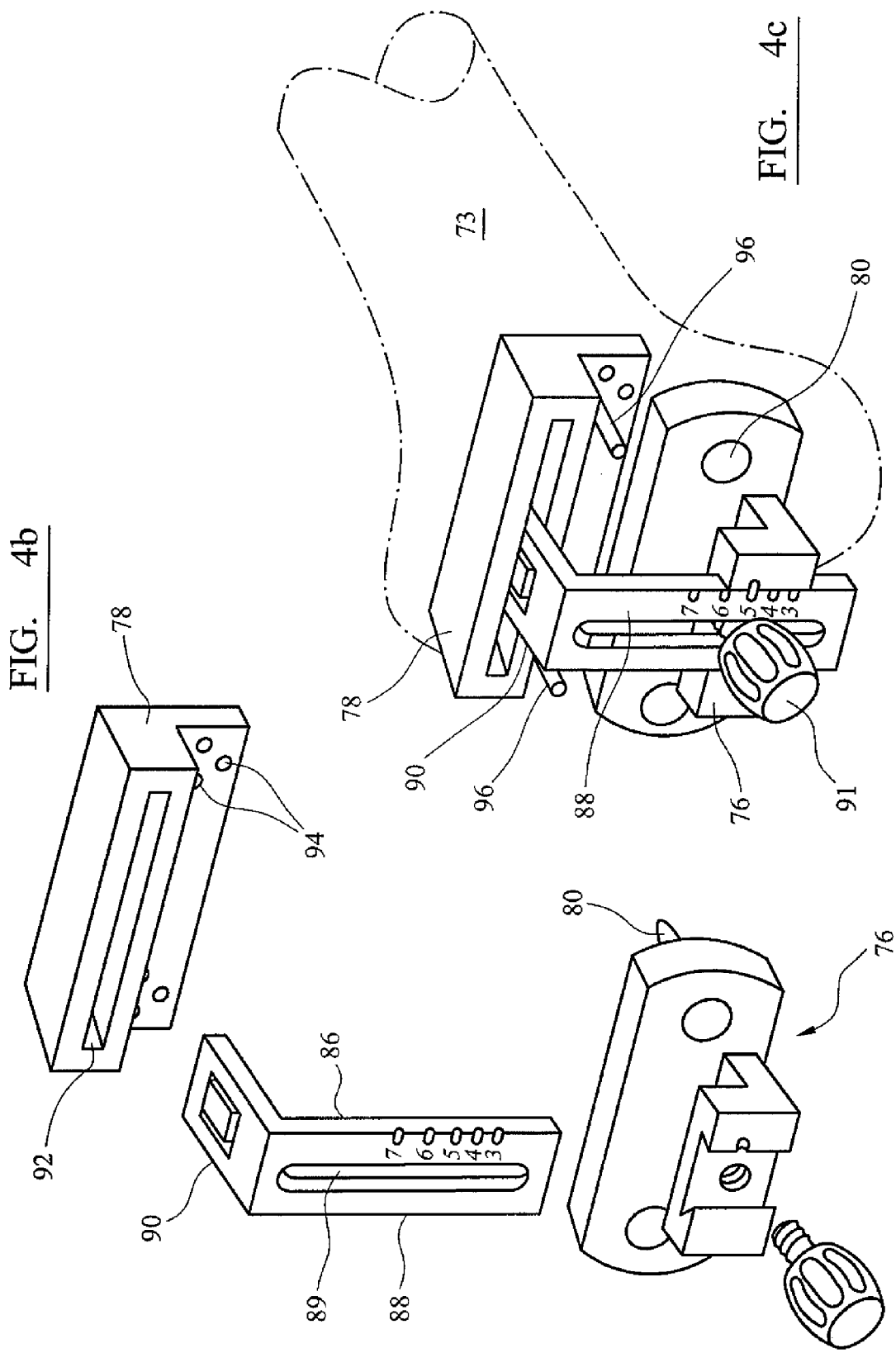

ORTHOPAEDIC CUTTING GUIDE INSTRUMENT

The present invention relates to a cutting guide instrument for use in a cutting step in an orthopedic surgical procedure.

A cutting guide instrument can be used in an orthopedic procedure to control the location and orientation of a cutting tool during a step of cutting a bone. This can be important to ensure that the bone is prepared accurately for fitting a prosthesis component in a subsequent step of the procedure.

The location and orientation of a cutting guide instrument can be determined manually, with reference to predetermined anatomical features on the patient's bone. For example, in the case of an instrument for determining the location and orientation of the plane for resecting the tibia in a knee replacement procedure, a cutting guide can be mounted on a reference rod which is fastened to the tibia by an ankle clamp to define the axis of the tibia. Such an instrument is available from DePuy Orthopedics Inc under the trade mark Specialist II. Accordingly, such manual instrument sets can include a reference component which is secured by a fixation element to the bone to be resected in a predetermined arrangement. The instrument set can then also include a cutting guide which can be fastened to the reference component and can provide the reference surface. The cutting guide can provide a reference surface which is engaged during the procedure by the cutting tool. The reference surface can be contacted by a saw (for example by its blade) in a resection step. A reference surface which is to be contacted by a saw can be flat, for example to define a resection plane. The reference surface can be provided by a bore, which can receive a rotating cutting tool such as a drill bit or a reamer.

The cutting guide can be fastened to the reference component by means of screw fasteners or by a clamp or by other attachment features. In order to position the reference surface of the cutting guide accurately relative to the reference component, it is important to control accurately the position of the reference surface in the cutting guide relative to the point of fastening to the reference component, whether by means of screw fasteners or a clamp or some other fastening feature. For example, the accuracy of the position and orientation of the reference surface can be affected by variations in the connection formed between the fixation element and the reference component and the connection formed between the attachment screws and the threaded bores provided by the reference component and the cutting block. Any variation in the dimensions, location, alignment and/or orientation of these features can result in the position and/or orientation of the reference surface of the cutting block being offset from the desired position and/or orientation.

The present invention provides a cutting guide instrument in which a reference component includes a locator arm, which engages the reference surface of a cutting block so that the reference component and cutting block are arranged in a predetermined manner.

Accordingly, in one aspect, the invention provides a cutting guide instrument for use in a cutting step in an orthopedic surgical procedure, which comprises:
a. a reference element which can be fixed to the bone aligned in a predetermined arrangement relative to the bone axis,
b. a cutting block which is separate from the reference element, and which has a reference surface which can be engaged by a cutting tool to define the location and orientation of the blade of the tool during the cutting step, and at least one fixation bore for receiving a fixation pin to fix the cutting block to the bone,
c. a locator arm which can be fastened to the reference element and can extend from the reference element to the cutting block where it can be fitted snugly against the reference surface in a pre-determined arrangement, so that the reference element and cutting block are arranged relative to one another in a predetermined arrangement in which the cutting block can be fixed to the bone by means of a fixation pin prior to separation of the reference element and the cutting block.

In another aspect, the invention provides a method of performing an orthopedic procedure using the cutting guide instrument comprising the steps of:
a. aligning the reference element relative to the bone; and
b. engaging the reference surface of the cutting block with the locator arm of the reference element so as to locate the cutting block relative to the bone.

The method can include a subsequent step of cutting the bone using a cutting instrument, which is located relative to the bone during the cutting step using the reference surface of the cutting block. The reference surface which is used during the cutting step is the same as the reference surface which is used to locate the cutting block relative to the reference step.

The locator arm directly engages the reference surface of the cutting block. The invention therefore has the advantage that the cutting block is positioned relative to the bone with direct reference to the reference surface. The invention therefore enables the surgeon accurately to control the position and/or orientation of the reference surface of the cutting block in order to take into account factors such as the patient's anatomy and implant type etc. The positions and/or locations of the reference component and/or first element are then adjusted to enable the cutting block to be secured in the desired position.

The invention therefore has the advantage that the accuracy with which the cutting guide is manufactured can be lower than is the case when the cutting block is engaged by a reference component other than on the reference surface. This can enable the cutting guide of the invention to be made by techniques that can be more efficient than are required in such known cutting blocks, for example by means of a casting technique.

The reference surface of the cutting block defines the location and orientation of the blade of the tool during the cutting step. The reference surface can be provided by an opening such as a slot or a bore which extends through the cutting block. The cutting block can be formed by casting. The at least one opening can then be formed after the cutting block has been cast. For example, the at least one opening can be formed in the cast cutting block using a wiring technique, which is similar to spark erosion. The wiring technique involves passing an electric discharge along a wire which extends through the cast cutting block. The electric discharge erodes the cutting block to provide an opening with the required dimensions. The wiring technique enables the dimensions of the opening to be accurately controlled.

It is recognised that the position of the or each opening within the cutting block might vary between cast cutting blocks. The invention however has the advantage that the positioning of the cutting block relative to the bone is controlled with reference to the position of the reference surface provided by the opening. The invention therefore does not require the position of the slot or other opening within the cutting block to be accurately controlled and therefore the cutting block can be formed by casting and the at least one opening can be formed using the wiring technique discussed above or some other cutting technique.

The locator arm is sufficiently dimensioned to be received within and engage the opening provided by the cutting block.

For example, the locator arm can comprise a plate portion which is sufficiently dimensioned to be received within and engage a slot provided by the cutting block. The plate portion can be a sliding fit in the slot of the cutting block. The invention has the advantage that the plate portion of the locator arm can be moved within the slot of the cutting block. This enables the surgeon to make minor adjustments to the position of the cutting block relative to the bone whilst the cutting block is located relative to the reference element. Preferably, the locator arm is a resilient tight fit in the opening in the cutting block so that unwanted relative movement between the locator arm and the cutting block is minimised. This can be arranged by means of a resiliently deformable tongue on the locator arm which is deformed when the arm is inserted into the opening.

An opening in the cutting block should be dimensioned so that the blade of a cutting instrument is a sliding fit therein. When the cutting instrument is a saw blade, the opening will be in the form of a slot. When the cutting instrument is a drill bit, the opening will be in the form of a bore. The appropriate design of such openings is well established.

For example, when the opening in the cutting block is in the form of a bore, the locator arm can have the form of a rod which is a sliding fit in the bore. It will generally be preferred for the cross-section of the rod to be approximately the same as the cross-section of the bore.

The reference surface can be provided by an external surface of the cutting block. The locator arm is dimensioned to contact the reference surface which is provided by a surface of the cutting block. The reference surface can provide an attachment feature which can cooperatively engage a further attachment feature which is provided by the locator arm. The locator arm can be a plate portion providing a protrusion which can fit in a groove provided in the reference surface of the cutting block. The reference surface can provide a groove which is shaped and dimensioned to receive and engage a plate portion of the locator arm.

The reference surface can be provided by a reference bore. The locator arm is sufficiently dimensioned to be received within and engage the reference bore of the cutting block. The locator arm can comprise a shaft portion having the a suitable cross-sectional shape and suitable cross-sectional dimensions to enable the shaft portion to be received within and engage the reference bore provided by the cutting block. The shaft portion of the locator arm can be a sliding fit in the reference bore of the cutting block. For example, the reference bore provided by the reference surface can have a circular cross-section and the locator arm can comprise a shaft portion having a circular cross-section.

The locator arm can extend at any angle relative to the reference element. The angle formed between the locator arm and the adjacent portion of the reference element can determine the angle of the resection cut of the bone.

Preferably, the portion of the locator arm which engages the reference surface of the cutting block extends at an angle of no more than 150°, more preferably no more than 120°, for example about 90° relative to the longitudinal axis of the adjacent portion of the reference element. Preferably, the portion of the locator arm which engages the reference surface of the cutting block extends at an angle of at least 30°, more preferably at least 60°, for example 75° relative to the longitudinal axis of the adjacent portion of the reference element.

The instrument of the invention can be arranged so that the angle between the first element and the locator arm is approximately equal to the angle between the axis of the bone and the plane on which the bone is to be cut.

The locator arm can be U-shaped. For example, a first branch of the U-shaped locator arm is dimensioned to engage the reference surface on the cutting block. The second branch extends substantially parallel to the first branch and can contact a further surface of the cutting block. The second branch can connect to the reference element. The first and second branches of the U-shaped locator arm may be equal in length or can have different lengths. The bridging portion of the U-shaped locator arm can contact a further surface of the cutting block.

The locator arm can be L-shaped. The first branch of the L-shaped locator arm can be dimensioned to be received within and engage the reference surface. The second branch can connect to the reference element. The angle between the first branch and the second branch can vary depending on the angle of the cut which is required to be made in the bone. The first and second branches of the L-shaped locator arm can have the same cross-sectional shape and dimensions or can have different cross-sectional shapes and dimensions. For example, the first branch of the L-shaped locator arm can be a plate portion having a substantially rectangular cross-section. The second branch of the L-shaped locator arm can be a shaft portion having a substantially circular cross-section. The first branch of the L-shaped locator arm can be a shaft portion having a circular cross-section. The second branch of the L-shaped locator arm can have a substantially rectangular cross-section.

When the locator arm is L-shaped or U-shaped, the second branch of the locator arm preferably extends either substantially parallel to or perpendicular to the longitudinal axis of the adjacent portion of the reference element.

The locator arm can be removably attached to the reference element. For example, the locator arm can be removably attached to the reference element by the size adjustment feature. The invention therefore has the advantage that the surgeon can select the type of locator arm which is required to be used for a particular procedure. For example, the surgeon can determine the shape and size of the locator arm which is required to be used for a particular procedure with a particular cutting block and for the particular angle of cut.

The shape of the reference element depends on the type of orthopedic procedure in which the instrument to be used. For example, when the instrument is to be used to perform the proximal tibial cut, the first element can be secured to the tibia, for example at the ankle, so that the reference component extends along the tibial axis. The locator arm can then be fastened relative to the first element at its proximal end.

When performing the distal femoral cut, the first element can be secured to the femur so that the reference element extends substantially along to the femoral axis. The locator arm can then be fastened relative to the reference element at its proximal end.

When performing the anterior femoral cut, the reference element can be secured to the femur on the distal resection plane, and located with respect to the intramedullary cavity. The reference element will then extend anteriorly from the femoral axis. The locator arm can then be fastened to this element and extend distally from it.

The reference element and the locator arm can be provided as separate pieces which can be assembled together, or can be moved relative to one another. The reference element and the locator arm can be provided as one piece.

The instrument can be configured so that the position of the locator arm can be adjusted relative to the reference component. This can enable the location of the cutting block to be varied according to the requirements of a patient. The locator arm and the reference element preferably provide mating male and female portions which provide sliding engagement between the locator arm and the reference element. The female portion is preferably provided by the locator arm and the male portion is preferably provided by the reference element. The mating male and female portions preferably contain a series of scale markings enabling the user to position the locator arm at the desired displacement relative to the reference element. Preferably, the adjustment feature enables the user to displace the locator arm along the longitudinal axis of the adjacent portion of the reference element. Alternatively, the adjustment feature can enable the user to displace the locator arm in a direction which forms an angle with the longitudinal axis of the adjacent portion of the reference element. The adjustment feature can enable the user to displace the locator arm in a direction which is substantially perpendicular to the longitudinal axis of the adjacent portion of the reference element.

The reference element preferably further comprises a locking shaft which engages the adjustment feature so as to secure the locator arm in the desired displacement relative to the reference element. The male portion of the adjustment feature preferably provides an opening. The female portion of the adjustment feature preferably provides a plurality of openings which are spaced apart from each other along the direction of the sliding engagement of the male and female portions of the adjustment feature. The locking shaft is preferably dimensioned and shaped to be received within the openings of the male and female portions of the adjustment feature.

The instrument will frequently be made from metallic materials. Materials which are known for the manufacture of surgical instruments can be used, including certain stainless steels.

Techniques for determining the appropriate location of the cutting block in accordance with the present invention include techniques which are conventional in known surgical procedures. For example, the location can be determined with reference to anatomical features, especially bone axes which are located using intramedullary or extramedullary rods. The appropriate position can be located using instruments which take references from other bone features. For example, the position of a cutting block might be determined with reference to the size of the patient's native bone, or to the size of the intended implant, or both, which can involve referencing the position of the cutting block with reference to bone surfaces, for example using a measurement instrument such as a stylus. The position of a cutting block can be determined using image data of the patient's bone. The position of a cutting block can be determined using navigated surgery techniques, as are known, for example using an array of reflectors or emitters which is fastened to one or more instrument components, and at least two cameras which can be used stereoscopically to determine the location and the orientation of the array.

In use, the surgeon can adjust the position of the locator arm, and the position of the reference surface of the cutting block, relative to the reference element by adjusting the adjustment feature. Once the locator arm has been positioned at the desired displacement relative to the reference element, the surgeon can insert the locking shaft through the opening provided by the reference element and through the aligned opening provided by the locator arm to secure the relative locations of the locator arm and the reference element.

Once the reference surface of the cutting guide has been positioned at the desired location with the desired orientation relative to a bone for a particular resection the cutting block can be attached to the bone by inserting at least one first element through the at least one fixation bore provided by the cutting guide. The locator arm can then be removed from engagement with the reference surface of the cutting guide. The surgeon can then perform the resection.

The present invention will now be described by way of example with reference to the accompanying drawings, in which:

FIGS. 4a to 4c illustrate a third embodiment of the instrument of the invention for determining the location and orientation of an anterior femoral cut.

Figure 1:
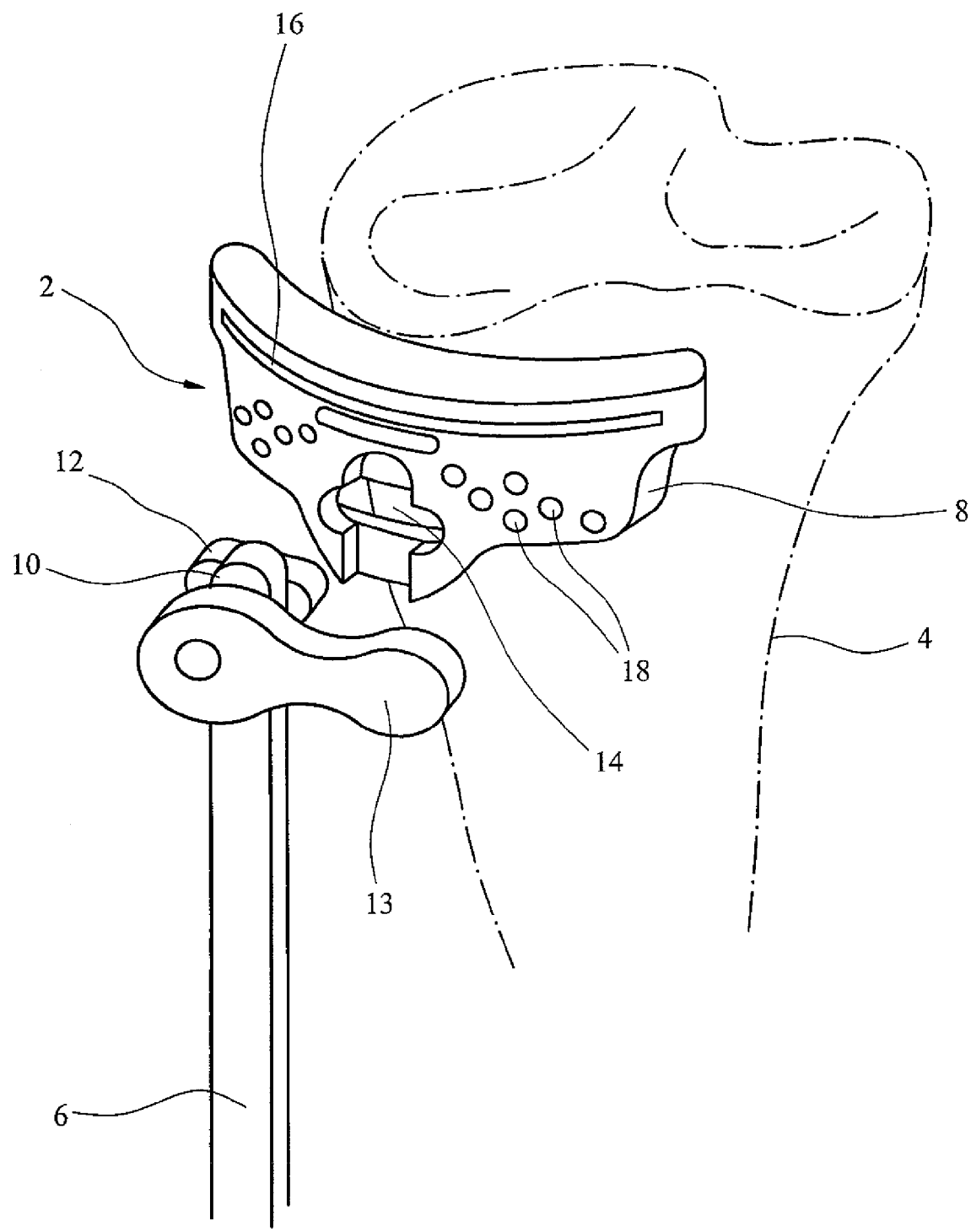
FIG. 1 is a view of a known instrument for determining the location and orientation of a proximal tibial cut.

FIG. 1 illustrates a known instrument 2 for determining the location and orientation of a proximal cut of a tibia 4. The known system 2 comprises a reference component 6 and a cutting guide block 8. The reference component and the cutting guide can be formed using conventional techniques for the manufacture of surgical instruments. The reference component 6 comprises an extramedullary alignment rod having an upper first end 10 and a lower second end (not shown). The first end 10 comprises a first attachment feature 12 in the form of a shaped plate. The attachment feature includes a lever 13 which can be used to rotate the plate around a pivot pin which extends through the rod and the plate. The rod has a first element at its lower second end, such as an ankle clamp (not shown). The cutting guide block 8 provides a slot 16 which provides the reference surface for referencing the location and orientation of the proximal cut. The cutting guide block 8 also comprises a second attachment feature in the form of an opening 14. The opening is shaped to receive the shaped plate 12 when the plate is in a first rotational position. The cutting block has an undercut which is accessed through the opening 14 so that, when the plate is rotated, it is engaged by the undercut and retained in the opening against withdrawal therefrom. The opening in the cutting guide block includes a groove in which the rod 6 can fit. The cutting guide block 8 provides a plurality of fixation bores 18.

In use, the extramedullary rod is secured to the patient's ankle by means of the ankle clamp or other element at the lower end of the rod. The rod 6 extends along the tibia so that the longitudinal axis of the rod 6 is aligned with the axis of tibia 4. The shaped plate 12 at the top of the rod 6 is positioned within the opening 14 in the cutting block 8, and rotated by means of the lever 13 so that it is held in the opening by means of the undercut. One or more fixation pins (not shown) are then inserted through the fixation bores 18 of the cutting guide block 8 to fasten the block to the tibia. The alignment rod 6 can then be detached from the cutting guide block by rotating the shaped plate 12 until it can be disengaged from the opening 14 in the block. The slot 16 providing the reference surface in the block is then positioned for performing the resection of the bone.

The location and orientation of the reference surface (not shown) provided by the slot 16 of the cutting guide 8 is therefore referenced by the reference component 6 relative to the tibia 4. The location and orientation of the reference surface (not shown) provided by the slot 16 will however be affected and altered by any variations in the dimensions of the cutting block and reference component as well as any errors in alignment resulting from the engagement of the attachment features 12 and 14 of the system. The possibility of the system containing any variations is reduced by using components which have been machined to have the precise dimensions required.

Figure 2A:
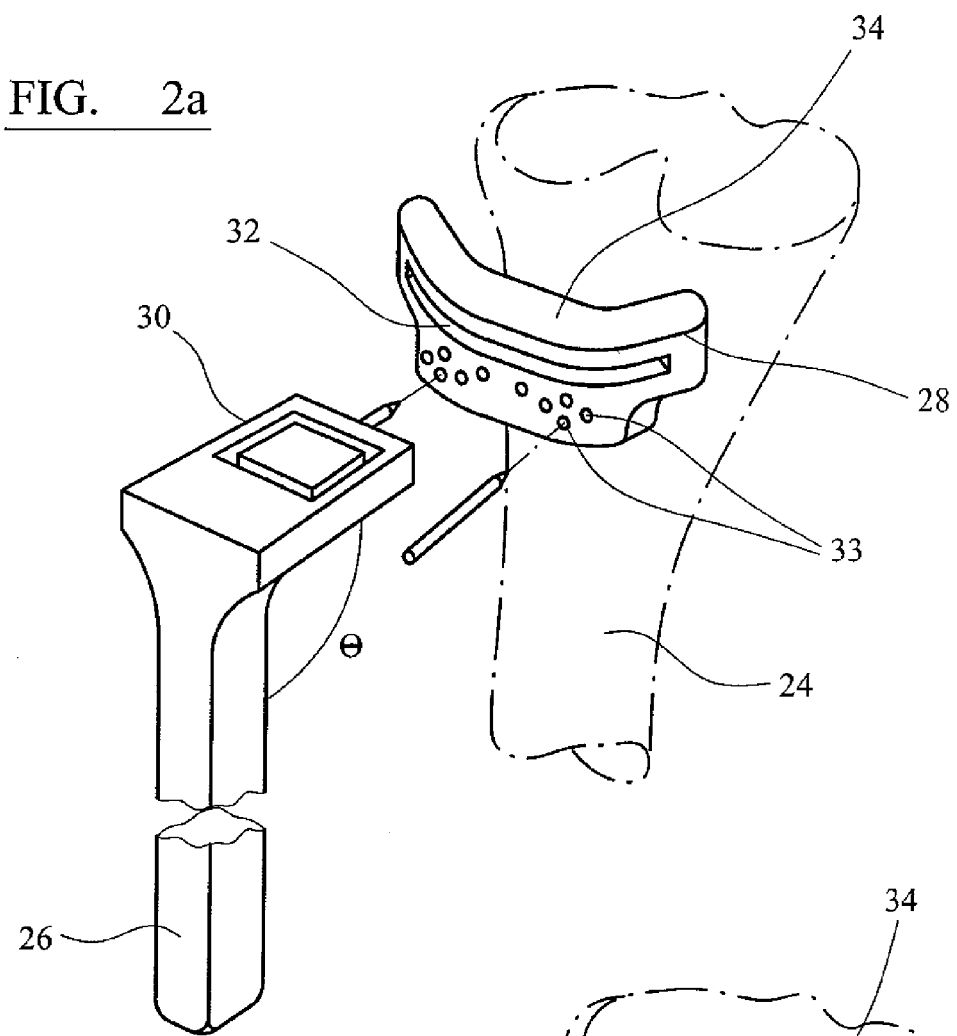
FIGS. 2a and 2b are isometric views of a first embodiment of the instrument of the invention for determining the location and orientation of a proximal tibial cut.
Figure 2B:
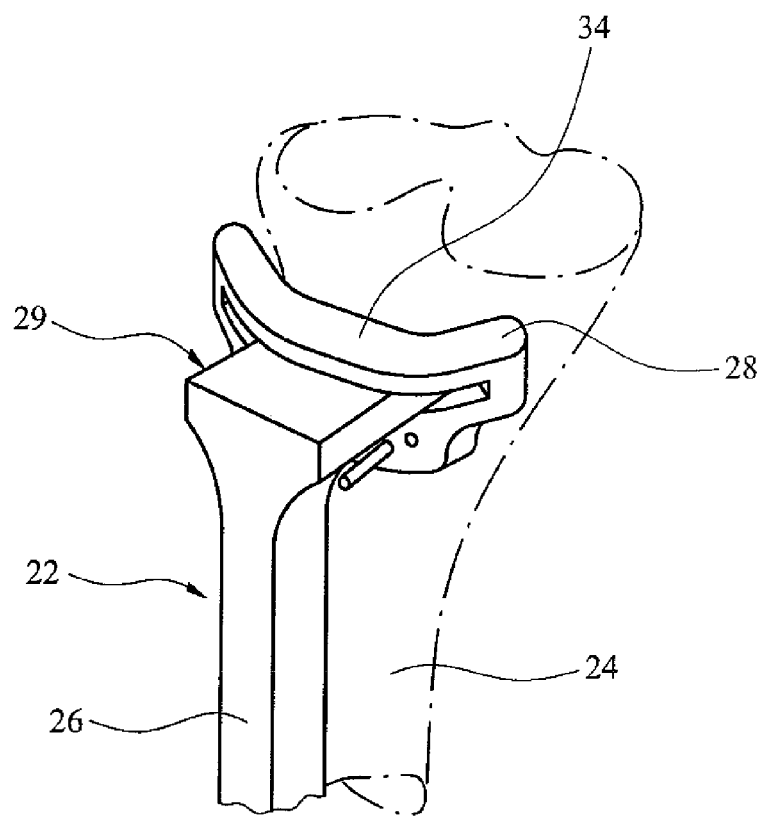

FIGS. 2a and 2b illustrate a first embodiment of the instrument 22 of the present invention for determining the location and orientation of a proximal cut of a tibia 24. FIG. 2a is an exploded view of the instrument, and FIG. 2b shows the assembled instrument. The instrument 22 comprises a reference component in the form an extramedullary rod 26 and a cutting guide block 28. The rod 26 has an upper first end 29 and a second end (not shown). The rod has a locator arm 30 at its upper first end. The rod 26 and the locator arm 30 are formed as a single unit. The locator arm 30 comprises a plate portion which extends from the first end 29 of the rod 26 at an angle θ to the longitudinal axis of the adjacent portion of the rod 26. The angle θ at which the plate portion of the locator arm 30 extends relative to the longitudinal axis of the adjacent portion of the rod 26 determines the angle θ of the cut relative to the longitudinal axis of the bone.

The cutting guide block 28 can be formed by casting. The cutting block 28 provides a slot 32 and a plurality fixation bores 33. The cutting block 28 also provides a reference surface 34 separate from the slot 32 for referencing the location and orientation of the proximal cut of the tibia 24. The reference surface 34 can provide a groove which extends parallel to the posterior-anterior axis of the tibia 24, which is shaped and dimensioned to receive and engage the plate portion of the locator arm 30 when mounted on the reference element 26.

In use, the rod 26 is secured to the patient's ankle at its lower end, for example using a conventional ankle clamp. The rod 26 extends along the tibia 24 so that the longitudinal axis (not shown) is aligned parallel to the axis of the tibia 24. The plate portion of the locator arm 30 is received within and engages the groove (not shown) provided by the reference surface 34 of the cutting block 28.

Alternatively, as shown in FIG. 2b, the plate portion of the locator arm 30 is inserted into the slot 32 of the cutting guide block.

The location and orientation of the tibial cut depends only on the separation of the locator arm 30 from the first element (not shown) and the angle θ formed between the locator arm 30 and the longitudinal axis of the adjacent portion of the reference component 26. The instrument 22 therefore has the advantage that the cutting block 28 is positioned relative to the tibia 24 with direct reference to the reference surface 34 or the slot 32. The surgeon can therefore accurately control the position and/or orientation of the cutting plane (defined by the reference surface 34 or the slot 32 according to surgeon preference).

Once the desired position and orientation of the cutting guide block 28 have been determined the surgeon inserts fixation screws or pins (generally two or more) into respective ones of the fixation bores 33. The surgeon disengages the locator arm 30 from the cutting block 28. The surgeon then performs the tibial cut, so that the posterior slope of the cut forms an angle θ with the tibial axis.

Figure 3A:
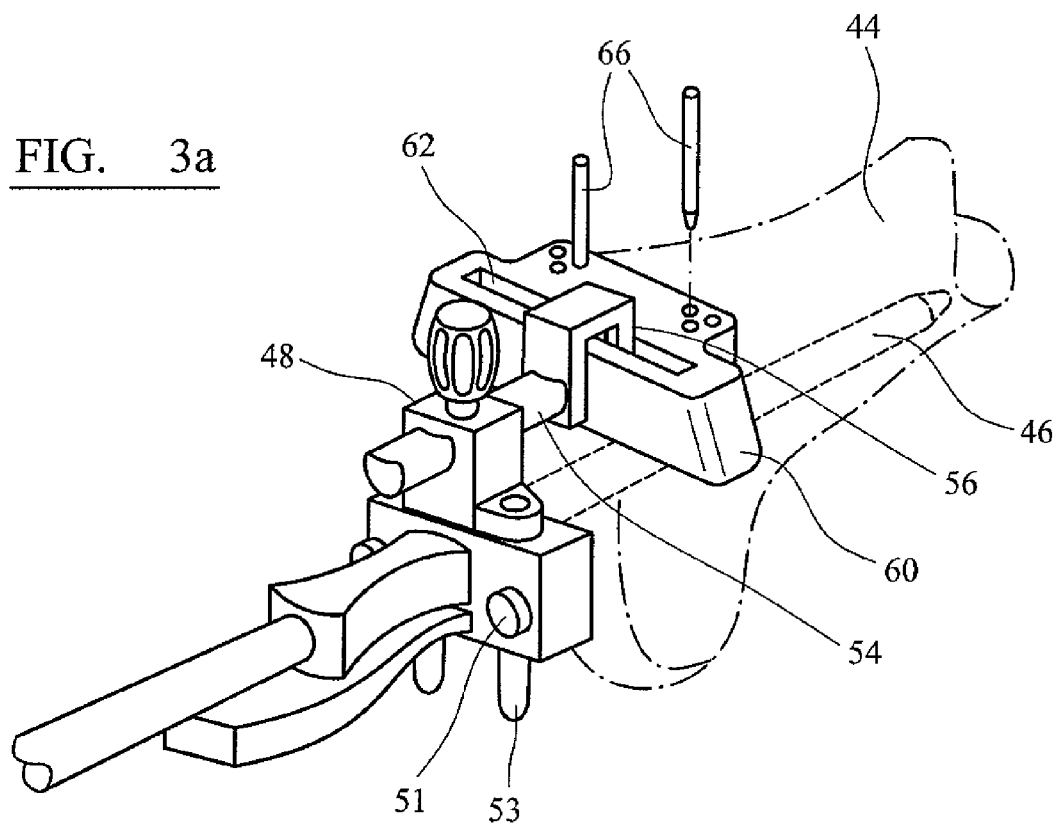
FIGS. 3a and 3b show a second embodiment of the instrument of the invention for determining the location and orientation of a distal femoral cut.
Figure 3B:
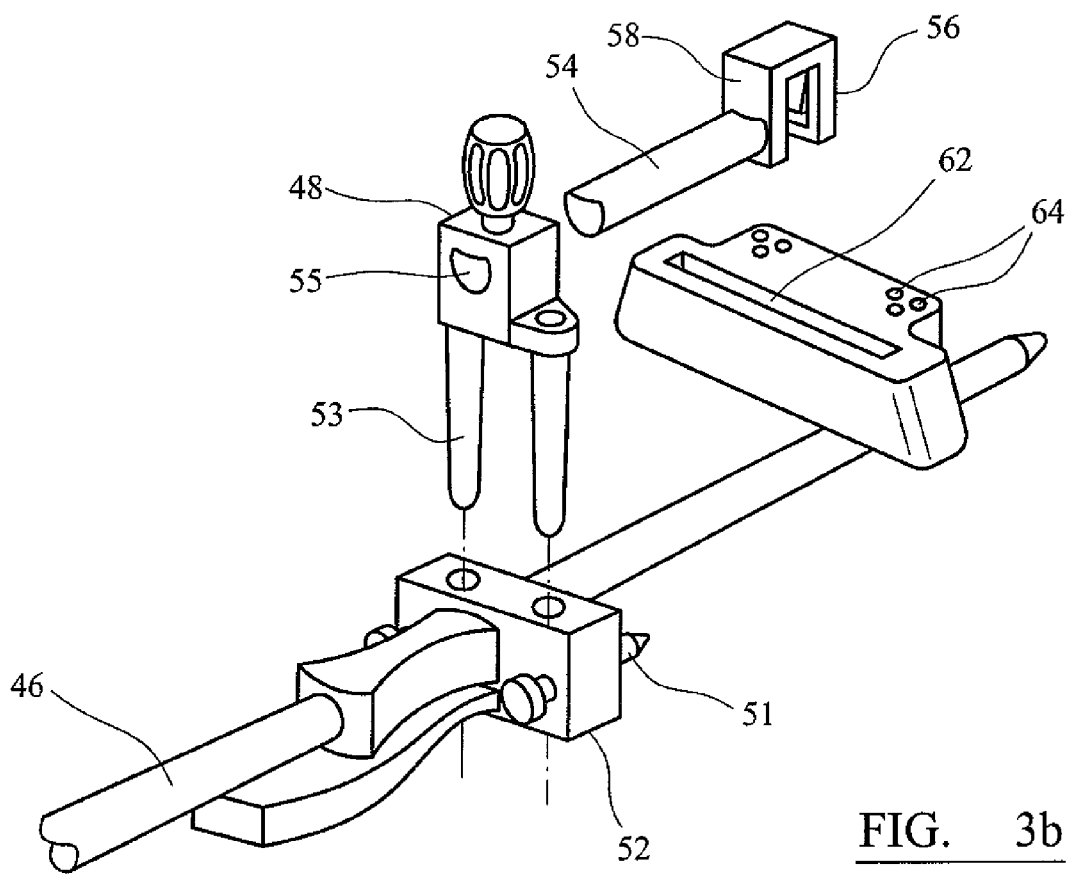

FIGS. 3a and 3b illustrate a second embodiment of the instrument 42 of the present invention for determining the location and orientation of a distal cut of a femur 44. FIG. 3a is an exploded view of the instrument, and FIG. 3b shows the assembled instrument. The instrument 42 comprises a reference element in the form of an intramedullary alignment rod 46. This extends along the medullary cavity within the femur, with a first end 48 within the cavity, and a second end 50 extending from within the cavity (which can be used as a handle to manipulate the instrument). The rod 46 has a block 52 fastened to it, with sharpened pins 51 which can penetrate bone tissue on the femoral condyles to prevent rotation of the rod about the axis defined by the rod.

An upstand 48 is mounted on the block 52 by means of rods 53 which fit into bores in the block 52. The upstand has a bore 55 extending through it.

A locator arm 54 can be inserted into the bore 55 in the upstand. The locator arm has a U-shaped bracket at one end, with a first arm 56 and a second arm 58. The second arm 58 extends substantially parallel to the first arm 56.

The instrument 42 comprises a cutting guide 60 which can be formed by casting. The cutting guide 60 has a slot 62 formed in it, and fixation bores 64. The reference surface of the cutting guide 60 is provided by the slot 62.

The instrument 42 includes one or more fixation pins 66 which are sized and shaped to be received within the fixation bores 64 of the cutting guide 60.

In use, the intramedullary rod 46 is inserted into the axial cavity within the femur, through an opening between the condyles. The block 52 is pushed against the condyles so that the sharpened pins 51 penetrate the condylar bone tissue. The upstand 48 is fitted to the block 52 by fitting the rods 53 into the bores in the block. The locator arm 54 is fitted to the upstand 48 by fitting it to the bore 55 therein.

The first arm 56 of the locator arm 54 is fitting into the slot 62 of the cutting guide 60. The engagement between the first arm 56 of the locator arm 54 and the slot determines the location and orientation of the slot cutting block 60 relative to the femur for guiding the distal femoral cut.

The instrument 42 has the advantage that the surgeon can accurately position and orientate the cutting block 60 with direct reference to the slot which is used to define the cutting plane.

The locator arm can be moved in translation parallel to the longitudinal axis which is defined by the bore 55 in the upstand, to position the cutting block 60 which is engaged by the locator arm in the desired location. Once the reference surface has been positioned in the desired location, the surgeon secures the cutting block in position.

Once the surgeon is satisfied that the cutting guide 60 is in the desired location with the desired orientation the surgeon inserts one or more attachment fixation pins 66 through the fixation bores 64 provided by the cutting guide 60. The locator arm 54 is then removed from engagement with the reference surface (not shown) provided by the slot 62 of the cutting guide 60. The surgeon can then perform the distal cut of the femur.

Figure 4A:
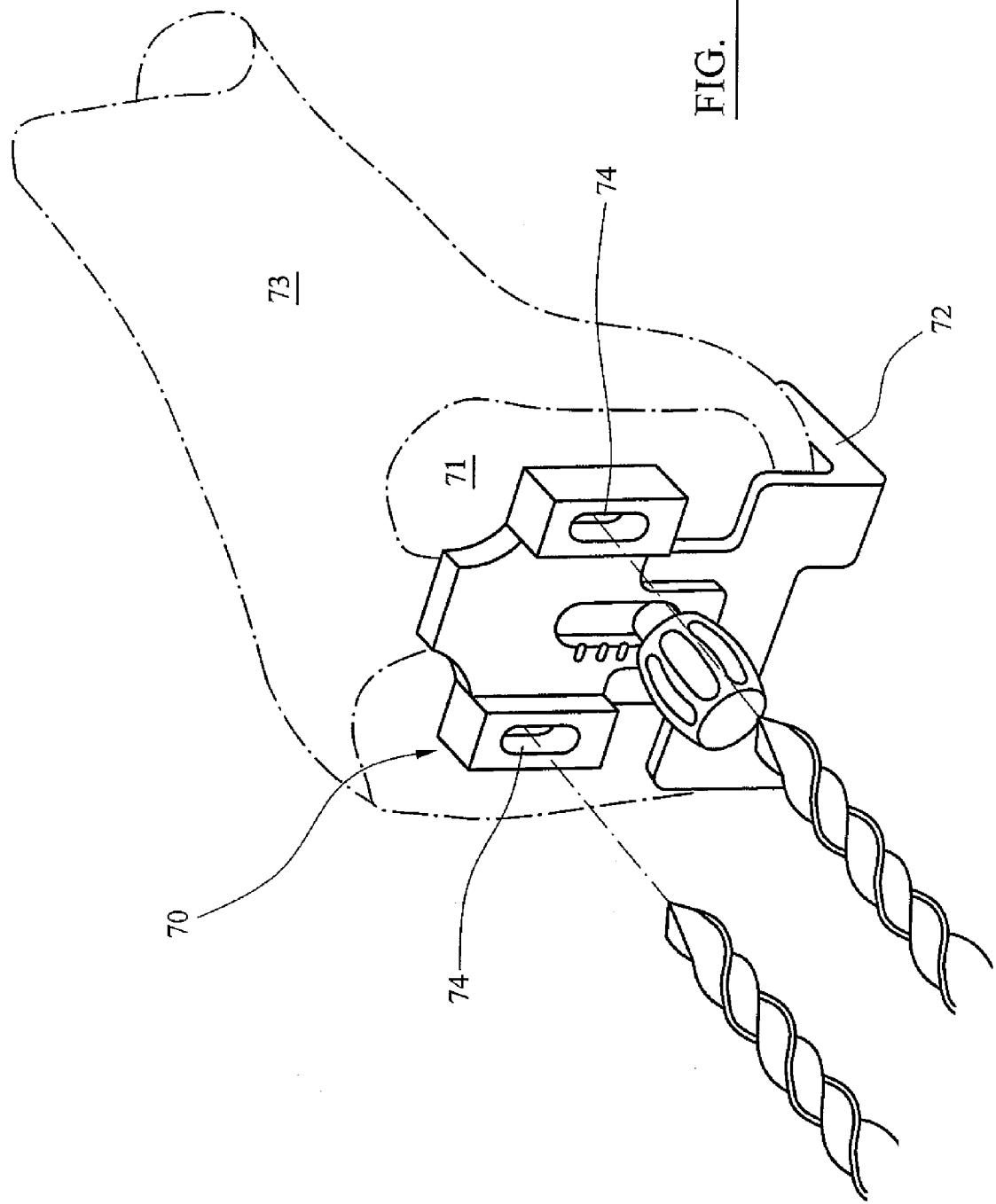

FIGS. 4a to 4c illustrate the use of the invention to determine the location and orientation of the anterior cut of the femur.

In an initial step which is illustrated in FIG. 4a, a drill guide 70 is placed against the distal face 71 of the femur 73. It is located along the anterior-posterior axis with reference to the posterior condyles using a locator component 72, which can also control the relative heights of the medial and lateral edges of the mounting plate (and therefore its orientation). The position of the drill guide is used to locate fixation holes for the instrument of the invention, by drilling bores in the bone through holes 74 in the plate as shown in FIG. 4a.

FIGS. 4b and 4c show the cutting guide instrument of the invention, which includes a mounting plate 76 and a cutting block 78. FIG. 4b is an exploded view of the instrument, and FIG. 4c shows the assembled instrument.

The instrument comprises a mounting plate 76 which is aligned with the bone as desired using the bores in the bone which are formed with reference to the drill guide 70. The mounting plate is fastened to the bone in this alignment using sharpened fixation pins 80.

The mounting plate has a bracket 82 extending from its front face, which has a groove 84 formed in it which has a dove-tailed cross-section. The instrument includes an L-shaped locator arm 86 with first and second limbs 88, 90. The first and second limbs are arranged so that they are approximately perpendicular to one another, although different angles between the first and second limbs can be used as appropriate to vary the angular relationship between the distal and anterior cuts. The first limb 88 of the arm 86 is a sliding fit in the groove 84. The first limb has a slot 89 formed in it which can receive a locking screw 91 to lock the arm against sliding in the groove in the plate.

The cutting block 76 has a slot 92 formed in it which provides a reference surface for determining the position and orientation of the anterior cut of the femur. The cutting block 76 also provides a plurality of fixation bores 94, which can receive fixation pins 96 for fastening the block to the femur.

The invention claimed is:

1. An assembly for use in a cutting step in an orthopedic surgical procedure involving a bone having a bone axis and a cutting tool having a blade, comprising: an alignment rod configured to be disposed at least partially within the intramedullary cavity of the bone, such that the alignment rod is aligned with the bone axis;
   a cutting block separate from the alignment rod, the cutting block having a slot defined at least in part by a reference surface configured to engage the blade of the cutting tool to define the location and orientation of the blade, and at least one fixation bore for receiving a fixation pin to fix the cutting block to the bone, the reference surface being perpendicular to the bone axis when the cutting block contacts the bone; and
   a locator arm having a proximal end and a distal end, the locator arm removably attached to and extending from the alignment rod at the proximal end and having a surface at the distal end that is configured to be at least partially disposed within the slot and removably engages the reference surface of the cutting block such that the alignment rod and the cutting block are arranged relative to one another in a predetermined arrangement;
   wherein the locator arm comprises a u-shaped bracket, the u-shaped bracket having a first arm sized and shaped to slidably engage the reference surface, and a second arm, substantially parallel to, and spaced apart from, the first arm, the first arm and the second arm connected by a bridge portion.

* * * * *